United States Patent
Caron et al.

(10) Patent No.: US 10,675,306 B2
(45) Date of Patent: Jun. 9, 2020

(54) ADRENOMEDULLIN THERAPY TO IMPROVE FETAL IMPLANTATION

(71) Applicant: The University of North Carolina at Chapel Hill, Chapel Hill, NC (US)

(72) Inventors: Kathleen M. Caron, Chapel Hill, NC (US); Brooke C. Matson, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/782,014

(22) PCT Filed: Dec. 8, 2016

(86) PCT No.: PCT/US2016/065544
§ 371 (c)(1),
(2) Date: Jun. 6, 2018

(87) PCT Pub. No.: WO2017/100413
PCT Pub. Date: Jun. 15, 2017

(65) Prior Publication Data
US 2018/0360890 A1    Dec. 20, 2018

Related U.S. Application Data

(60) Provisional application No. 62/264,616, filed on Dec. 8, 2015.

(51) Int. Cl.
*A61K 35/54* (2015.01)
*A61K 38/22* (2006.01)
*A61K 38/17* (2006.01)
*A61K 38/20* (2006.01)

(52) U.S. Cl.
CPC .......... *A61K 35/54* (2013.01); *A61K 38/1709* (2013.01); *A61K 38/1793* (2013.01); *A61K 38/22* (2013.01); *A61K 38/2093* (2013.01)

(58) Field of Classification Search
None
See application file for complete search history.

(56) References Cited

U.S. PATENT DOCUMENTS

| | | | |
|---|---|---|---|
| 7,504,096 B1 | 3/2009 | Stewart et al. | |
| 7,659,081 B2 | 2/2010 | Cuttitta et al. | |
| 2018/0141989 A1* | 5/2018 | Pioszak | C07K 14/575 |

FOREIGN PATENT DOCUMENTS

| | | |
|---|---|---|
| EP | 1205185 A1 | 5/2002 |
| RU | 2444315 C1 | 3/2012 |

OTHER PUBLICATIONS

Cai et al., Regulatory Peptides, 2005; 129: 125-132 (Year: 2005).*
Martinez et al. Biochem. J., 2004; 383: 413-418 (Year: 2004).*
Matson et al., 2017; Biology of Reproduction; 97: 466-477 (Year: 2017).*
DeCherney "In vitro fertilization and embryo transfer: a brief review", Yale J. Biol. Med. 59(4):409-414 (1986) (Abstract Only) 2 pages.
Li et al. "Haploinsufficiency for Adrenomedullin Reduces Pinopodes and Diminishes Uterine Receptivity in Mice", Biol. Reprod. 79(6):1169-1175 (2008).
Notification of Transimttal of the International Search Report and the Written Opinion of the International Searching Authority, or the Declaration corresponding to International Application No. PCT/US2016/065544 dated Mar. 30, 2017.
Notification Concerning Transmittal of International Preliminary Report on Patentability corresponding to International Application No. PCT/US2016/065544 dated Jun. 21, 2018.
Chauhan et al. "Potential role of intermedin/adrenomedullin 2in early embryonic development in rats", Regulatory Peptides 170:65-71 (2011).
Chauhan et al. "Admomedullin2 (ADM2)/Intermedin (IMD) in Rat Ovary: Changes in Estrous Cycle and Pregnancy and Its Role in Ovulation and Steroidogenesis", Biology of Reproduction 92(2):39, 1-9 (2015).
Extended European Search Report corresponding to European Application No. 16873825.0 dated May 27, 2019.
Li et al. "Reduced maternal expression of adrenomedullin disrupts fertility, placentation, and fetal growth in mice", The Journal of Clinical Investigation 116(10):2653-2662 (2006).
Yotsumoto et al. "Expression of Adrenomedullin, a Hypotensive Peptide, in the Trophoblast Giant Cells at the Embryo Implantation Site in Mouse", Developmental Biology 203:264-275 (1998).

* cited by examiner

*Primary Examiner* — Christina M Borgeest
(74) *Attorney, Agent, or Firm* — Myers Bigel, P.A.

(57) ABSTRACT

The present invention relates to methods of improving blastocyst implantation by delivering adrenomedullin to the endometrium of a subject. The invention further relates to methods of performing in vitro fertilization.

19 Claims, 4 Drawing Sheets
Specification includes a Sequence Listing.

*SD(a,b,c,d)*  
UNEVEN SPACING  
HIGH SD

*SD(e,f,g,h)*  
EVEN SPACING  
LOW SD

SEQUENCE LISTING

<160> NUMBER OF SEQ ID NOS: 1

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gly Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

ADRENOMEDULLIN THERAPY TO IMPROVE FETAL IMPLANTATION

Cross Reference to Related Applications

This application is a 35 U.S.C. § 371 national phase application of PCT Application PCT/US2016/065544 filed Dec. 8, 2016, which claims priority under 35 § 119(e) to U.S. Provisional Application No, 62/264,616, filed Dec. 8, 2015, the entire contents of each of which are incorporated herein by reference in its entirety.

Statement Regarding Electronic Filing Of A Sequence Listing

A Sequence Listing in ASCII text format, submitted under 37 C.F.R. § 1.821, entitled 5470-764_ST25.txt, 893 bytes in size, generated on May 25, 2018 and filed via EFS-Web, is provided in lieu of a paper copy. This Sequence Listing, is hereby incorporated by reference into the specification for its disclosures.

FIELD OF THE INVENTION

The present invention relates to methods of improving blastocyst implantation by delivering adrenomedullin to the endometrium of a subject. The invention further relates to methods of performing in vitro fertilization.

BACKGROUND OF THE INVENTION

In vitro fertilization (IVF) techniques have been available for many years and IVF is the most effective form of assisted reproductive technology. However, IVF success rates are low, with live birth rates ranging from about 40% for women under 35 to about 4% for women over 42. Many factors influence the success rate, including maternal age, duration of infertility or subfertility, number of oocytes, hormone levels, body mass index, endometrium characteristics, and semen quality. Failure to achieve proper implantation of the blastocyst is one of the major issues in both natural and assisted reproduction.

Adrenomedullin (Adm gene, AM protein) is a peptide vasodilator that is elevated nearly five-fold in healthy human pregnancies but often blunted in pregnancies that are complicated by fetal growth restriction, gestational diabetes, or preeclampsia. Polymorphisms in the genes encoding AM peptide or its G protein-coupled receptor CLR have been shown to be associated with poor pregnancy outcomes, including altered birth weight, gestational diabetes, and preeclampsia (Lenhart et al., *Am. J. Perinatol.* 31:327 (2014)). Moreover, studies have demonstrated that plasma concentrations of MR-proADM (a proteolytic byproduct and surrogate of AM peptide) are blunted in severe preeclampsia and that MR-proADM is similarly effective as other common preeclampsia biomarkers (endoglin and placental growth factor) at discriminating between patients with severe preeclampsia and normotensive patients (Matson et al., *Placenta* 35:780 (2014)). Therefore, maintaining high levels of AM peptide signaling during human pregnancy is critical for good maternal and fetal clinical outcomes (Lenhart et al., *Trends Endocrinol. Metab.* 23:524 (2012)).

Using gene-targeted mouse models, it has been shown that haploinsufficiency for maternal AM leads to poor uterine receptivity, reduced pinopode formation, and subfertility (Li et al., *Biol. Reprod.* 79:1169 (2008)). Pregnant $Adm^{+/-}$ females exhibit abnormal implantation spacing, ectopic placentation, and fetal growth restriction that is largely independent of fetal genotype (Li et al., *J. Clin. Invest.* 116:2653 (2006)). These data indicate that a modest genetic reduction in maternal levels of AM is sufficient to cause pregnancy complications. Although $Adm^{+/-}$ mice die at mid-gestation with lymphatic vascular defects (Fritz-Six et al., *J. Clin. Invest.* 118:40 (2008)), it has recently been discovered that fetal AM is required for branching morphogenesis of the placental labyrinth layer and remodeling of maternal spiral arteries. $Adm^{+/-}$ fetal vessels are larger and under-branched compared to those of their wildtype littermates. The maternal spiral arteries which feed the $Adm^{+/-}$ placenta fail to remodel compared to the spiral arteries of neighboring $Adm^{+/+}$ placentas. Importantly, these phenotypes are reversed in a genetic model with 3-fold overexpression of fetal AM. Concomitantly, a marked reduction in uterine natural killer (uNK) cells was found along with a significant change in the placental chemokine and cytokine profile of $Adm^{+/-}$ placentas. Furthermore, in response to AM treatment, uNK cells secrete a variety of chemokines and cytokines that work to increase MMP9 activity and induce smooth muscle cell apoptosis. Therefore, AM serves as a trophoblast-derived factor that is critical for fetal placental vascularization and for enabling the maternal vascular adaptation to pregnancy to protect against preeclampsia (Li et al., *J. Clin. Invest.* 123:2408 (2013)).

There is a need in the art for new methods for enhancing fetal implantation and increasing the success rate of in vitro fertilization.

SUMMARY OF THE INVENTION

While the vasodilator activity of AM was known and a potential role for AM in treatment of preeclampsia has been proposed, a direct effect of AM on blastocyst implantation has not previously been identified. The present invention is based on the finding that short-term treatment of the uterus with AM prior to pregnancy improves the fetal implantation rate and overall quality of implantation. This simple and minimally-invasive procedure may be used to improve the success of assisted reproductive technologies.

Thus, one aspect of the invention relates to a method of improving blastocyst implantation in the endometrium of a mammalian subject in need thereof, comprising locally delivering to the endometrium of the subject an effective amount of AM or an analog or functional fragment thereof, thereby improving blastocyst implantation.

A further aspect of the invention relates to a method of increasing the likelihood of blastocyst implantation in the endometrium of a mammalian subject in need thereof, comprising locally delivering to the endometrium of the subject an effective amount of adrenomedullin or an analog or functional fragment thereof, thereby increasing the likelihood of blastocyst implantation.

Another aspect of the invention relates to a method of increasing the success rate of in vitro fertilization in a mammalian subject in need thereof, comprising locally delivering to the endometrium of the subject an effective amount of AM or an analog or functional fragment thereof and a blastocyst, thereby increasing the success rate of in vitro fertilization.

An additional aspect of the invention relates to a method of performing in vitro fertilization in a mammalian subject in need thereof, comprising locally delivering to the endometrium of the subject an effective amount of AM or an analog or functional fragment thereof and a blastocyst, thereby performing in vitro fertilization.

A further aspect of the invention relates to a formulation comprising AM and a pharmaceutically acceptable carrier, wherein the formulation is in a form suitable for localized delivery to the endometrium of a mammalian subject.

These and other aspects of the invention are set forth in more detail in the description of the invention below.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The transitional phrase "consisting essentially of" means that the scope of a claim is to be interpreted to encompass the specified materials or steps recited in the claim and those that do not materially affect the basic and novel characteristic(s) of the claimed invention. The term "consisting essentially of," as applied to a polypeptide sequence of this invention, means a polypeptide that consists of both the recited sequence (e.g., SEQ ID NO) and a total of ten or less (e.g., 1, 2, 3, 4, 5, 6, 7, 8, 9, or 10) additional amino acids on the N-terminal and/or C-terminal ends of the recited sequence such that the function of the polypeptide is not materially altered. The total of ten or less additional amino acids includes the total number of additional amino acids on both ends added together. The term "materially altered," as applied to polypeptides of the invention, refers to an increase or decrease in vasodilation activity of at least about 50% or more as compared to the activity of a polypeptide consisting of the recited sequence.

As used herein, the term "polypeptide" is a sequence of amino acids and encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

The present invention is based on the finding that short-term treatment of the uterus with AM prior to pregnancy improves the fetal implantation rate and overall quality of implantation. This simple and minimally-invasive procedure may be used to improve the success of assisted reproductive technologies.

Thus, one aspect of the invention relates to a method of improving blastocyst implantation in the endometrium of a mammalian subject in need thereof, comprising locally delivering to the endometrium of the subject an effective amount of AM or an analog or functional fragment thereof, thereby improving blastocyst implantation.

The phrase "improving blastocyst implantation" as used herein refers to an improvement in any characteristic of the blastocyst implantation relative to the characteristic in the absence of the methods of the present invention. Characteristics of blastocyst implantation include, without limitation, number of blastocysts implanted, spacing of implanted blastocysts, vascularization, uterine receptivity, pinopode (uterodome) formation, blastocyst invasion through the endometrial epithelium, improvement in decidualization, and improvement in fetal protection from maternal rejection. In some embodiments, the improvement in implantation allows a smaller number of blastocysts to be administered, e.g., during in vitro fertilization procedures, to achieve at least the same success rate, which in turn may lead to a decrease in multiple pregnancies as well as more efficient procedures.

Another aspect of the invention relates to a method of increasing the likelihood of blastocyst implantation in the endometrium of a mammalian subject in need thereof, comprising locally delivering to the endometrium of the subject an effective amount of AM or an analog or functional fragment thereof, thereby increasing the likelihood of blastocyst implantation. In some embodiments, the likelihood of blastocyst implantation is increased by at least about 5% or more, e.g., at least about 5%, 10%, 15%, 20%, 25%, 30%, 40%, 50%, or more.

In some embodiments of the invention, the subject is one that is undergoing in vitro fertilization and the AM or an analog or functional fragment thereof enhances the implantation of a blastocyst that is externally delivered to the subject. As used herein, the term "externally delivered" means that the blastocyst has been previously removed from the subject or from another mammal and later is delivered to the subject. In other embodiments of the invention, the subject is not undergoing in vitro fertilization and the AM or an analog or functional fragment thereof enhances the implantation of a blastocyst that is internally delivered to the subject. As used herein, the term "internally delivered" means that the blastocyst is delivered to the endometrium of the subject internally, i.e., by natural travel from the ovary without being removed from the subject.

An additional aspect of the invention relates to a method of increasing the success rate of in vitro fertilization in a mammalian subject in need thereof, comprising locally delivering to the endometrium of the subject an effective amount of AM or an analog or functional fragment thereof and a blastocyst, thereby increasing the success rate of in vitro fertilization. The success rate of in vitro fertilization can be calculated in many ways, including without limitation the percentage of pregnancies or the percentage of live births. The increase in success rate is relative to the success rate in the absence of the methods of the invention and encompasses an increase in any measurement of success. In some embodiments, the success rate is increased by at least about 5% or more, e.g., at least about 5%, 10%, 15%, 20%, 25%, 30%, 40%, 50%, or more.

A further aspect of the invention relates to method of performing in vitro fertilization in a mammalian subject in need thereof, comprising locally delivering to the endometrium of the subject an effective amount of AM or an analog or functional fragment thereof and a blastocyst, thereby performing in vitro fertilization.

Human AM is a 52 amino acid peptide with one intramolecular disulfide bond. AM is initially expressed as a longer precursor (185 amino acids in humans). The amino acid sequence of human AM (SEQ ID NO:1) and AM from other mammalian species is well known in the art and can be found in databases such as GenBank. Examples of sequences are shown in Table 1.

SEQ ID NO:1 Human adrenomedullin
YRQSMNNFGG LRSFGCRFGT CTVQKLAHQI YQFT-DKDKDN VAPRSKISPQ GY

TABLE 1

| Species | Precursor length | GenBank Accession No. |
| --- | --- | --- |
| Homo sapiens | 185 | AAC60632.1 |
| Canis lupus familiaris | 188 | AAD09957.1 |
| Rattus norvegicus | 185 | BAA03665.1 |
| Sus scrofa | 188 | BAA03590.1 |
| Mus musculus | 184 | EDL16987.1 |
| Bos Taurus | 188 | DAA22195.1 |
| Pan troglodytes | 185 | JAA36350.1 |

A "fragment" of AM is an amino acid sequence of reduced length relative to full length AM and comprising, consisting essentially of, and/or consisting of an amino acid sequence of contiguous amino acids identical to AM. In some embodiments, such fragments can comprise, consist essentially of, and/or consist of peptides having a length of at least about 4, 6, 8, 10, 12, 15, 20, 25, 30, 35, or 40 or more consecutive amino acids of AM. In other embodiments, such fragments can comprise, consist essentially of, and/or consist of peptides having a length of no more than about 4, 6, 8, 10, 12, 15, 20, 25, 30, 35, or 40 consecutive amino acids of AM.

A "functional fragment" of AM is a fragment that substantially retains at least one biological activity normally associated with AM (e.g., vasodilator activity, protein binding, receptor binding). In particular embodiments, the "functional fragment" substantially retains all of the activities possessed by the unmodified peptide. By "substantially retains" biological activity, it is meant that the fragment retains at least about 50%, 60%, 75%, 85%, 90%, 95%, 97%, 98%, 99% or more, of the biological activity of full length AM (and can even have a higher level of activity than AM). Biological activities such as protein binding and vasodilation activity can be measured using assays that are well known in the art and as described herein. Examples of functional fragments of AM include, without limitation, the following amino acids of SEQ ID NO:1: 27-52, 25-52, 24-52, 23-52, 13-52, 32-40, 28-40, 32-52, and 30-52.

An "analog" of AM is a polypeptide or other molecule which differs from naturally occurring AM by minor modifications to the naturally occurring polypeptide, but which substantially retains at least one biological activity normally associated with AM (e.g., vasodilator activity, protein binding, receptor binding). In particular embodiments, the "analog" substantially retains all of the activities possessed by the unmodified peptide. Minor modifications include, without limitation, changes in one or a few amino acid side chains (e.g., 1, 2, 3, 4, or 5 amino acids), changes to one or a few amino acids (including deletions, insertions, and/or substitutions) (e.g., 1, 2, 3, 4, or 5 amino acids), changes in stereochemistry of one or a few atoms (e.g., 1, 2, 3, 4, or 5 atoms), and minor derivatizations, including, without limitation, methylation, glycosylation, phosphorylation, acetylation, myristoylation, prenylation, palmitoylation, amidation, PEGylation, and addition of glycosylphosphatidyl inositol. By "substantially retains" biological activity, it is meant that the analog retains at least about 50%, 60%, 75%, 85%, 90%, 95%, 97%, 98%, 99%, or more, of the biological activity of AM (and can even have a higher level of activity than AM). Biological activities such as protein binding and vasodilation activity can be measured using assays that are well known in the art and as described herein. Analogs of AM are well known in the art and are described, for example, in U.S. Pat. Nos. 9,062,123; 7,314,856; and 6,320,022; and US Publication Nos. 2015/0258176; 2014/0287984; and 2014/0100163; each of which is incorporated by reference in its entirety.

Analogs of AM include peptides and fragments of the invention that are modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by any suitable methods. For example, one or more non-naturally occurring amino acids, such as D-alanine, can be added to the termini. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Additionally, the peptide terminus can be modified, e.g., by acetylation of the N-terminus and/or amidation of the C-terminus. Likewise, the peptides can be covalently or noncovalently coupled to pharmaceutically acceptable "carrier" proteins prior to administration.

In some embodiments of the invention, the AM is delivered to the endometrium concurrently with the blastocyst. As used herein, the term "concurrently" means sufficiently close in time to produce a combined effect (that is, concurrently can be simultaneously, or it can be two or more events occurring within a short time period before or after each other). In other embodiments, the AM is delivered to the endometrium before delivery of the blastocyst, e.g., no more than about 24 hours prior to delivery of the blastocyst, e.g., no more than about 24, 20, 18, 16, 14, 12, 10, 9, 8, 7, 6, 5, 4, 3, 2, or 1 hour, or no more than about 30, 20, 15, 10, or 5 minutes before delivery of the blastocyst. In some embodiments, the AM is delivered to the endometrium after delivery of the blastocyst, e.g., no more than 5, 4, 3, 2, or 1 day after delivery of the blastocyst, e.g., before the inner cell mass starts to differentiate.

In some embodiments, the AM is delivered to the endometrium more than one time, e.g., 2, 3, 4, 5, or more times, in any combination before, concurrently with, or after delivery of the blastocyst. In some embodiments, AM is delivered multiple time after the blastocyst is delivered, e.g., during the time period between delivery and implantation of the blastocyst, e.g., every 0.5, 1, 2, 3, 4, 5, 6, 8, 10, or 12 hours after delivery of the blastocyst for about 24 to 48 hours.

In certain embodiments, the AM is delivered together with other factors. In some embodiments, the AM is delivered together with complement factor H or another binding protein that stabilizes or otherwise protects AM from degradation. In certain embodiments, the AM is delivered together with at least one additional agent or technique that improves blastocyst implantation. Examples of suitable additional agents include, without limitation, leukemia inhibiting factor, interleukin-6, Stat3 modulators, connexin 43 modulators, delivery nanoparticles, or agents that selectively inhibit the binding of AM to alternate receptor conformations present in the uterine tissue In one embodiment, an additional technique is damaging (e.g., scratching) of the endometrium, e.g., concurrently with the implantation procedure or in the previous estrous cycle prior to implantation.

In the methods of the invention AM is locally delivered to the endometrium, as distinguished from systemic (e.g., intravenous) administration. Local delivery of AM avoids side effects of systemic delivery such as decreased blood pressure, as well as permitting much lower doses of AM to achieve a beneficial effect.

The AM can be locally delivered to the endometrium by any suitable method known in the art. In some embodiments, the AM is delivered by intravaginal administration, e.g., by use of a catheter. In some embodiments, the AM delivered by uterine injection.

As used herein, the term "subject" refers to humans and other mammals. Thus, veterinary treatment is provided in accordance with the present invention. As such, the present invention provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), and the like.

A subject in need of the methods of the present invention is a subject that has experienced or is experiencing infertility or subfertility issues. In some embodiments, the subject has a nonreceptive uterus or a uterus with decreased receptiveness. A "nonreceptive uterus" is one that that does not result in proper blastocyst implantation. In some embodiments, the subject is one that does not respond to hormone therapies for preparing and priming the uterus during assisted reproduction. In some embodiments, the subject has a deformed uterus that interferes with implantation.

In some embodiments, the subject is one that has normal plasma levels of AM. In other embodiments, the subject has lower than normal plasma levels of AM, e.g., less than 90%, 80%, 70%, 60%, or 50% of normal levels. "Normal plasma levels of AM" as used herein refers to the average plasma level in the population of subjects under the same conditions (e.g., gender, pregnancy status, disease status). Typical plasma AM levels in non-pregnant humans is about 5-20 pmol/L and increases about five-fold during pregnancy. In some embodiments, the subject has an AM deficiency due to polymorphisms and/or mutations in the Adm gene or in one or more genes encoding AM receptors.

As a further aspect, the invention provides pharmaceutical formulations and methods of administering the same to achieve any of the effects (e.g., improved blastocyst implantation) described above. The pharmaceutical formulation may comprise any of the reagents described above in a pharmaceutically acceptable carrier, e.g., AM or functional fragment or analog thereof. In some embodiments, the pharmaceutical formulation may further comprise additional agents, including without limitation, complement factor H and/or at least one additional agent that improves blastocyst implantation as described above. In certain embodiments, the formulation is in a form suitable for localized delivery to the endometrium of a mammalian subject.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The peptides of the invention can be formulated for administration in a pharmaceutical carrier in accordance with known techniques. See, e.g., Remington, The Science And Practice of Pharmacy (21$^{st}$ Ed. 2006). In the manufacture of a pharmaceutical formulation according to the invention, the peptide (including the physiologically acceptable salts thereof) is typically admixed with, inter alia, an acceptable carrier. The carrier can be a solid or a liquid, or both, and may be formulated with the peptide as a unit-dose formulation which can contain from 0.01 or 0.5% to 95% or 99% by weight of the peptide. One or more peptides can be incorporated in the formulations of the invention, which can be prepared by any of the well-known techniques of pharmacy.

For injection, the carrier will typically be a liquid, such as sterile pyrogen-free water, sterile normal saline, hypertonic saline, pyrogen-free phosphate-buffered saline solution, bacteriostatic water, or Cremophor EL[R] (BASF, Parsippany, N.J.). These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use. Encapsulation of the peptides in a suitable delivery vehicle, e.g., polymeric particles (e.g., microparticles or nanoparticles) or implantable devices (e.g., depot or sustained-release formulations) may increase the efficiency of delivery.

Further, the present invention provides liposomal formulations of the peptides disclosed herein and salts thereof. The technology for forming liposomal suspensions is well known in the art. When the peptide or salt thereof is an aqueous-soluble salt, using conventional liposome technology, the same can be incorporated into lipid vesicles. In such an instance, due to the water solubility of the peptide or salt, the peptide or salt will be substantially entrained within the hydrophilic center or core of the liposomes. The lipid layer employed can be of any conventional composition and can either contain cholesterol or can be cholesterol-free. When the peptide or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the peptides disclosed herein or salts thereof, can be lyophilized to produce a lyophilizate which can be reconstituted with a pharmaceutically acceptable carrier, such as water, to regenerate a liposomal suspension.

In the case of water-insoluble peptides, a pharmaceutical composition can be prepared containing the water-insoluble peptide, such as for example, in an aqueous base emulsion. In such an instance, the composition will contain a sufficient amount of pharmaceutically acceptable emulsifying agent to emulsify the desired amount of the peptide. Particularly useful emulsifying agents include phosphatidyl cholines and lecithin.

In particular embodiments, the peptide is administered to the subject in an effective amount, as that term is defined above. Dosages of pharmaceutically active peptides can be determined by methods known in the art, see, e.g., Remington's Pharmaceutical Sciences (Mack Publishing Co., Easton, Pa.). The effective dosage of any specific peptide will vary somewhat from peptide to peptide, and patient to patient, and will depend upon the condition of the patient and the route of delivery. As a general proposition, a dosage from about 0.001 mg to about 100 mg or more will have efficacy, with all weights being calculated based upon the weight of the peptide, including the cases where a salt is employed.

Having described the present invention, the same will be explained in greater detail in the following examples, which are included herein for illustration purposes only, and which are not intended to be limiting to the invention.

EXAMPLE 1

Effect of Adrenomedullin on Implantation

It was hypothesized that administration of AM, an endocrine factor critical for a healthy pregnancy, to female mice would improve uterine receptivity and implantation rates. To test this hypothesis, vehicle, AM (150 pmol), or AM (150 pmol)+AM(24-50) (2 nmol), a CLR (AM receptor) antagonist, was injected directly into the lumen of each uterine horn of BalbC mice on day 2.5 of pseudopregnancy. Five to ten minutes post-treatment, eight fertilized blastocysts were injected into each horn. Dams were euthanized three days later, and the number and spacing of the viable implantation sites were evaluated. Notably, the uterine horns treated with AM had significantly more embryo implantation sites which were evenly distributed throughout the length of the horn (FIGS. 1A-1D). The mechanism underlying this improvement is unknown, but preliminary data suggest that AM has a potent effect on cell junction organization in the uterine epithelium, which is critical for remodeling of the uterus during implantation and may have consequences for fertility.

Using this conceptually simple but elegant in vivo experiment, it was concluded that delivery of AM directly into the uterine lumen prior to the establishment of pregnancy promotes blastocyst implantation. This conclusion was arrived at by quantitating the number and spacing of viable implantation sites in uterine horns that were treated with either vehicle or AM prior to blastocyst transfer. AM-treated uteri had significantly more viable implantation sites three days post-transfer compared to vehicle-treated uteri. Furthermore, these implantation sites were more evenly distributed throughout the length of the horn a sign of improved receptivity and embryo viability (FIGS. 1A-1D).

Figure 1A:
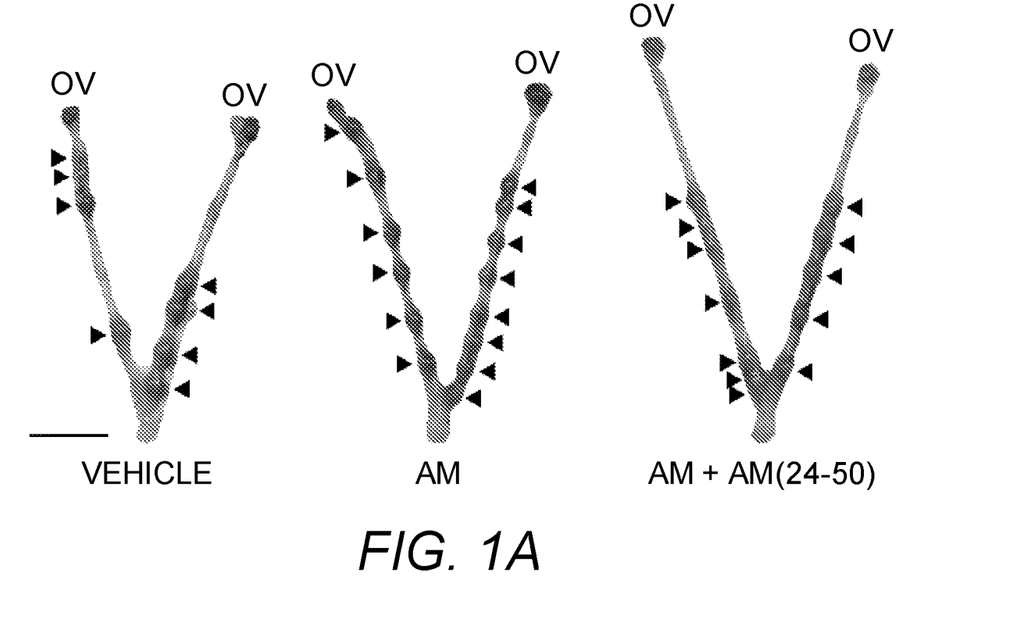
FIGS. 1A-1D show AM improves implantation success and spacing in mice. A, Images of e6.5 embryos within uteri treated with vehicle, AM, or AM+AM(24-50) prior to transfer of 8 blastocysts per horn. Arrowheads indicate viable implantation sites as determined by uptake of Evans blue dye. Scale bar, 1 cm. B, Quantitation of viable implant sites per horn. ns, not significant. *$p<0.05$, Mann-Whitney test. C, Illustration of quantitation method for spacing of e6.5 embryos within uterine horns. SD, standard deviation. D, Quantitation of spacing using method depicted in (C). *$p<0.05$, unpaired t test.
Figure 1B:
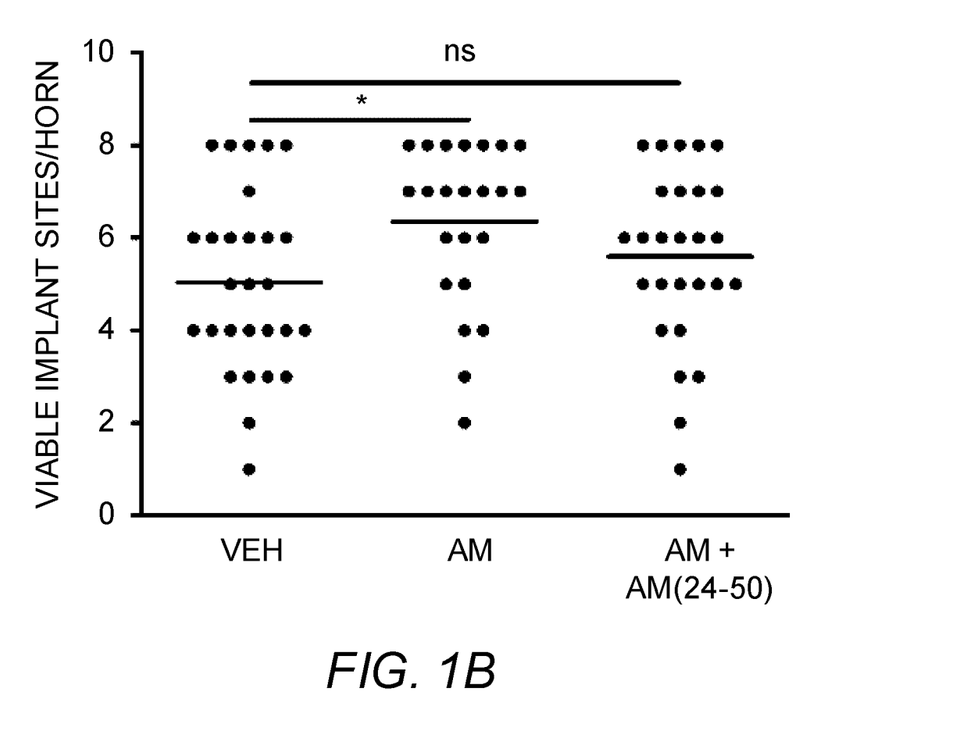
Figure 1C:
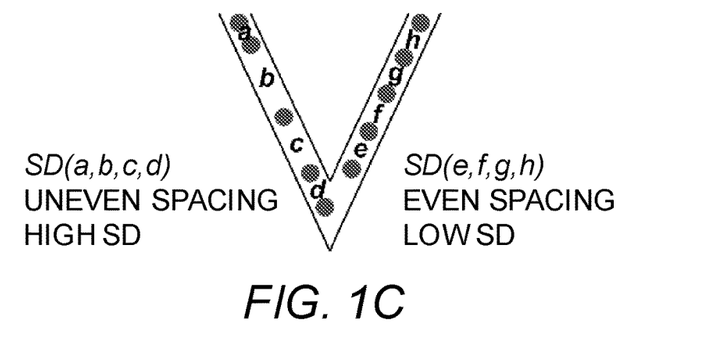
Figure 1D:
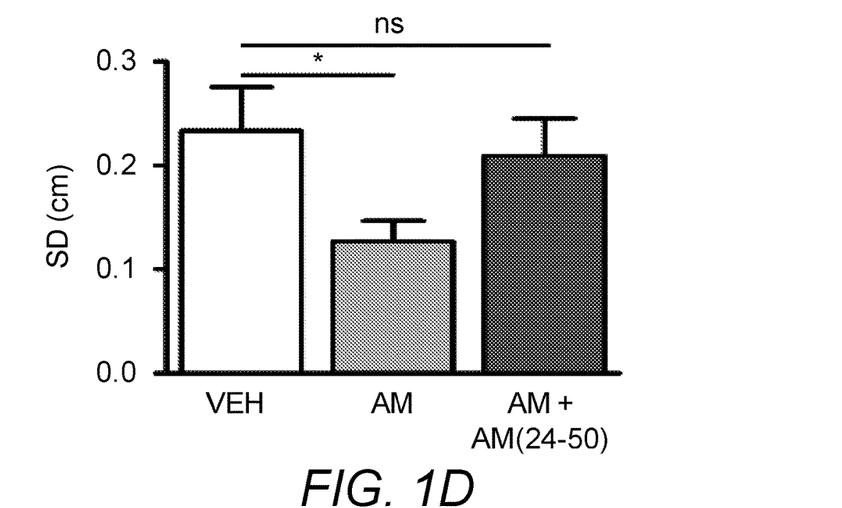
Figure 2:
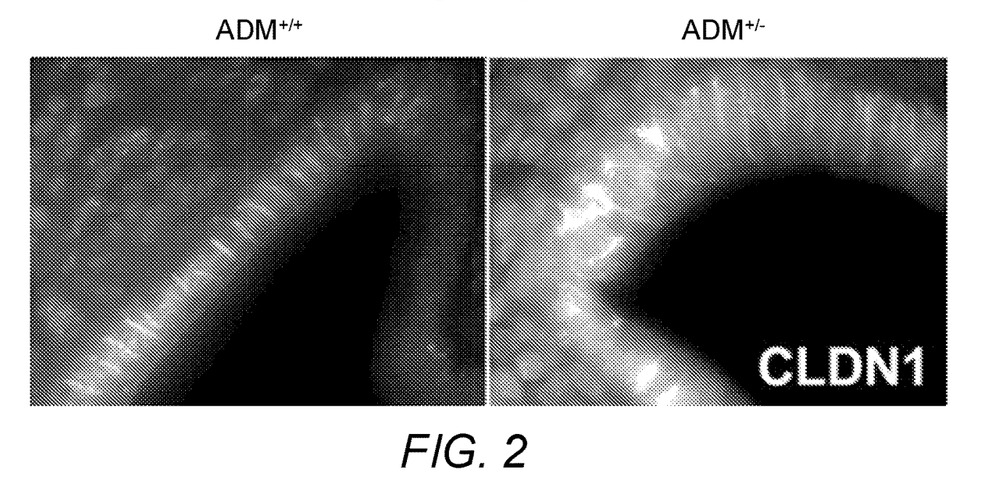
FIG. 2 shows AM promotes organization of tight junction protein CLDN1 in uterine epithelium. Immunofluorescence for tight junction protein CLDN1 was performed on e5.5 inter-implantation sites from wild-type and Adm heterozygote dams.
Figure 3A:
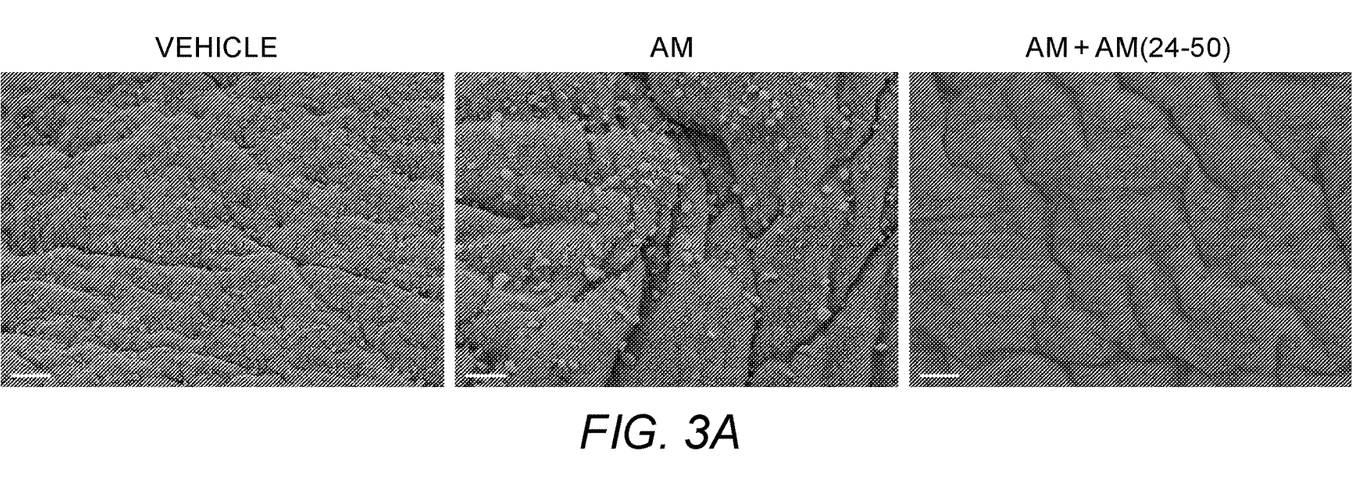
FIGS. 3A-3D show AM promotes pinopode formation and size. A, Scanning electron micrographs of pinopodes in wild type uteri treated with vehicle, AM, or AM+AM(24-50) for 30 minutes. Scale bars, 5 μm. B-D, Quantitation of pinopodes per field (B), size (C), and percent area of field (D). n=3 animals, n>4 fields per animal. ***$p<0.001$, unpaired t test.
Figure 3B:
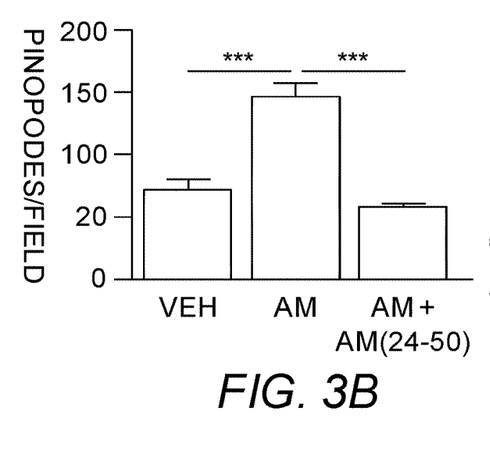
Figure 3C:
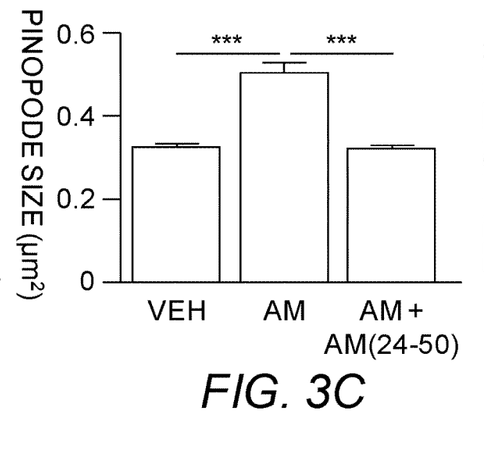
Figure 3D:
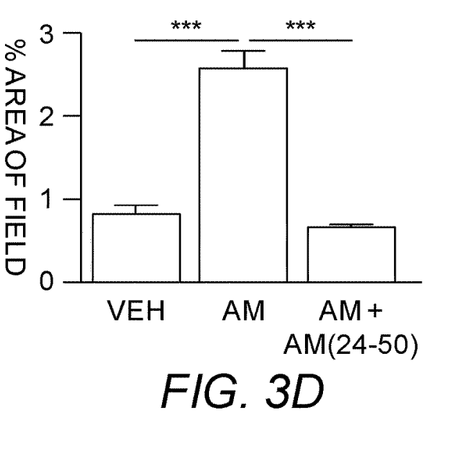

Notably, aberrant uterine epithelial remodeling is associated with implantation defects in vivo. Therefore, proper spatiotemporal expression and organization of cell junction proteins is critical for compliance of uterine epithelial and stromal compartments with blastocyst-derived cues and may have consequences for fertility. To determine whether AM can promote cell junction organization between uterine epithelial cells in vivo, which could potentially explain improved implantation rates with AM delivery, immunofluorescence was performed for a tight junction protein, claudin 1 (CLND1), in archived wild-type and $Adm^{+/-}$ e5.5 inter-implantation sites. Interestingly, collapse of CLDN1 to the basolateral side of the luminal epithelium was observed in $Adm^{+/-}$ inter-implantation sites, suggesting that full dosage of maternal AM is critical for maintaining uterine epithelial polarization (FIG. 2).

The effect of AM on pinopode formation and size was studied. Wild-type mice were treated with vehicle, AM (150 pmol), or AM (150 pmol)+AM(24-50) (2 nmol) for 30 min and the amount and size of pinopodes was quantitated (FIGS. 3A-3D). The results demonstrated that AM promotes pinopode formation and size.

Figure 4A:
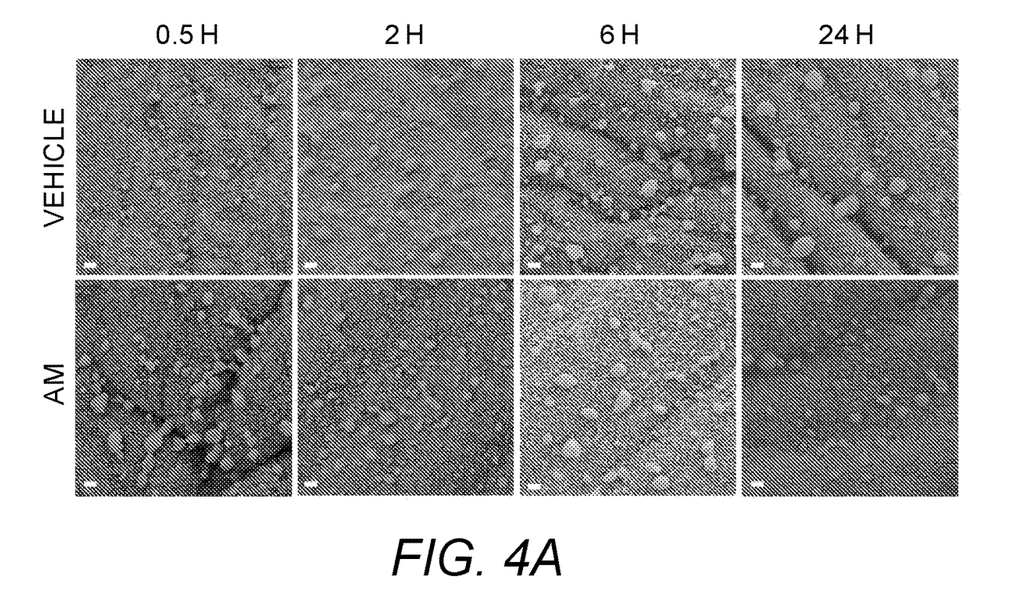
FIGS. 4A-4B show AM accelerates pinopode formation in wild type mice between days 2.5-3.5 of pseudopregnancy. A, Scanning electron micrographs of vehicle- and AM-treated uteri throughout treatment time course. Scale bars, 1 μm. B, Quantitation of pinopodes per field throughout treatment time course. *$p<0.05$ at indicated time point, unpaired t test.
Figure 4B:
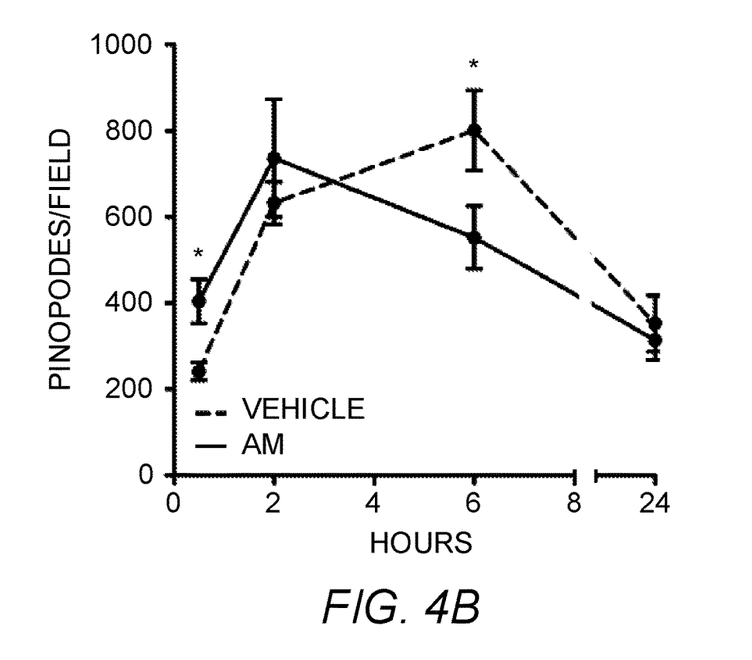

Further studies were performed to measure the effect of AM (150 pmol) on the rate of pinopode formation. The number of pinopodes was quantitated throughout a time course of AM treatment in wild-type mice (FIGS. 4A-4B). The results show that AM treatment accelerates pinopode formation.

The foregoing is illustrative of the present invention, and is not to be construed as limiting thereof. The invention is defined by the following claims, with equivalents of the claims to be included therein.

We claim:

1. A method of increasing the likelihood of blastocyst implantation in the endometrium of a mammalian subject in need thereof, comprising locally delivering to the endometrium of the subject an effective amount of adrenomedullin or an analog or functional fragment thereof, thereby increasing the likelihood of blastocyst implantation;
    wherein the analog comprises a change to 5 or fewer amino acid side chains, a deletion, insertion, and/or substitution of 5 or fewer amino acids, a change in stereochemistry of 5 or fewer atoms, a derivatization selected from methylation, glycosylation, phosphorylation, acetylation, myristoylation, prenylation, palmitoylation, amidation, PEGylation, and/or addition of glycosylphosphatidyl inositol, and/or addition of a blocking agent at the amino- and/or carboxyl-terminal ends wherein the blocking agent facilitates survival of said analog in vivo; and
    wherein the functional fragment is selected from amino acids 27-52, 25-52, 24-52, 23-52, 13-52, 32-40, 28-40, 32-52, or 30-52 of SEQ ID NO:1.

2. The method of claim 1, wherein the subject is undergoing in vitro fertilization and the method further comprises externally delivering a blastocyst to the endometrium of the subject.

3. The method of claim 1, wherein the subject is not undergoing in vitro fertilization and the method further comprises internally delivering a blastocyst to the endometrium from the ovary of the subject.

4. The method of claim 1, wherein the adrenomedullin is delivered to the endometrium concurrently with the blastocyst.

5. The method of claim 1, wherein the adrenomedullin is delivered to the endometrium no more than 24 hours prior to delivery of the blastocyst.

6. The method of claim 1, wherein the adrenomedullin is delivered to the endometrium no more than 1 hour prior to delivery of the blastocyst.

7. The method of claim 1, wherein the adrenomedullin is delivered to the endometrium no more than 5 days after delivery of the blastocyst.

8. The method of claim 1, wherein adrenomedullin is delivered to the subject more than once before, during, and/or after delivery of the blastocyst.

9. The method of claim 1, wherein the adrenomedullin is delivered together with complement factor H.

10. The method of claim 1, further comprising delivering at least one additional agent or technique that improves blastocyst implantation.

11. The method of claim 1, wherein the adrenomedullin is delivered by intravaginal administration.

12. The method of claim 1, wherein the adrenomedullin is delivered using a catheter.

13. The method of claim 1, wherein the adrenomedullin is delivered by uterine injection.

14. The method of claim 1, wherein the subject is a human.

15. The method of claim 1, wherein the subject has experienced or is experiencing fertility issues.

16. The method of claim 1, wherein the subject has a nonreceptive uterus.

17. The method of claim 1, wherein the subject has normal plasma levels of adrenomedullin.

18. The method of claim 1, wherein the subject has lower than normal plasma levels of adrenomedullin.

19. A method of performing in vitro fertilization in a mammalian subject in need thereof, comprising locally delivering to the endometrium of the subject an effective amount of adrenomedullin or an analog or functional fragment thereof and a blastocyst, thereby performing in vitro fertilization:
wherein the analog comprises a change to 5 or fewer amino acid side chains, a deletion, insertion, and/or substitution of 5 or fewer amino acids, a change in stereochemistry of 5 or fewer atoms, a derivatization selected from methylation, glycosylation, phosphorylation, acetylation, myristoylation, prenylation, palmitoylation, amidation, PEGylation, and/or addition of glycosylphosphatidyl inositol, and/or addition of a blocking agent at the amino- and/or carboxyl-terminal ends wherein the blocking agent facilitates survival of said analog in vivo; and
wherein the functional fragment is selected from amino acids 27-52, 25-52, 24-52, 23- 52, 13-52, 32-40, 28-40, 32-52, or 30-52 of SEQ ID NO:1.

* * * * *

UNITED STATES PATENT AND TRADEMARK OFFICE
CERTIFICATE OF CORRECTION

PATENT NO.         : 10,675,306 B2
APPLICATION NO.    : 15/782014
DATED              : June 9, 2020
INVENTOR(S)        : Caron et al.

Page 1 of 1

It is certified that error appears in the above-identified patent and that said Letters Patent is hereby corrected as shown below:

In the Specification

Column 3, Line 31: Please correct "n>4" to read -- $n \geq 4$ --

Signed and Sealed this
Twenty-seventh Day of October, 2020

Andrei Iancu
*Director of the United States Patent and Trademark Office*